United States Patent [19]

Green

[11] Patent Number: 4,978,049
[45] Date of Patent: Dec. 18, 1990

[54] THREE STAPLE DRIVE MEMBER
[75] Inventor: David T. Green, Westport, Conn.
[73] Assignee: United States Surgical Corporation, Norwalk, Conn.
[21] Appl. No.: 358,547
[22] Filed: May 26, 1989
[51] Int. Cl.⁵ .......................................... A61B 17/072
[52] U.S. Cl. .................................... 227/178; 227/21; 227/30; 227/180
[58] Field of Search ...................... 227/19, 20, 21, 30, 227/178, 180; 606/75

[56] References Cited
U.S. PATENT DOCUMENTS
3,079,606 3/1963 Bobrov et al. .
3,252,643 5/1966 Strekopytov et al. .
3,490,675 1/1970 Green et al. .
3,499,591 3/1970 Green .
4,633,874 1/1987 Chow et al. .................... 227/19
4,767,044 8/1988 Green ............................ 227/19

Primary Examiner—Douglas D. Watts
Assistant Examiner—Rinaldi Rada
Attorney, Agent, or Firm—Thomas R. Bremer; Dilworth, Peter G.; Rocco S. Barrese

[57] ABSTRACT

A staple drive member for a surgical stapling apparatus. The staple drive member is capable of driving up to three staples at a time and comprises a body portion having a camming surface at its proximal end contacted by a transversely moving cam, and three rectangular staple pusher plates oriented in a staggered arrangement such that two outside plates are located predominantly at the proximal end, and one middle plate is located predominantly at the distal end.

14 Claims, 6 Drawing Sheets

THREE STAPLE DRIVE MEMBER

BACKGROUND OF THE INVENTION

1. Field of the Invention

This invention relates to surgical stapling apparatus, and more specifically to a drive member within a surgical stapler for driving a surgical staple into body tissue.

2. Description of the Prior Art

Surgical stapling apparatus are widely used in surgical procedures to fasten body tissue quickly and efficiently by drivings fasteners, or staples into the tissue. In certain types of staplers, such as those for mechanically stitching together hollow organs, the main linear drive, a cam member, moves transversely to the direction the staples are to be driven. Typically such staplers employ a number of staple drive members or pusher elements located in grooved slots of a staple retaining cartridge and arranged end to end in rows. Under normal operation the transversely moving cam contacts a cam surface on the drive member thereby pushing the staple driver down the grooved slot. The drive member transmits linear motion from the driving cam to the staples. The rows of staples are thereby driven into the body tissue to be fastened.

An example of such a drive member is illustrated in Green et al. U.S. Pat. No. 3,490,675. The drive member disclosed therein has a pusher plate, guide rails, and a V-shaped portion for contacting the driving cam.

A further modification is illustrated in Green U.S. Pat. No. 3,499,591, which discloses a two staple driver. It is more advantageous to be able to drive double rows of staples with a single cam stroke instead of single rows since a double row of staples will have greater holding strength. The two staple driver disclosed therein is an integral piece construction comprising two drive sections in separate planes, with a V-shaped top surface for contacting the pusher cam. Each staple pair is staggered longitudinally (i.e., each staple is positioned diagonally behind the other, in a zig-zag fashion) and bridges the push-bar path.

When the Green '591 double pusher ejects two staples to engage tissue, the forces generated tend to be balanced in both the side-to-side and front-to-back directions, thereby decreasing the offset loadings on the pushers and reducing their tendency to bind. The tips of the pusher bars in Green '591 used to move the pusher and eject staples are arranged, relative to the pushers, so that the maximum force that must be exerted during the formation of staples into a B-shape occurs at only one staple pair at a time. This is accomplished by staggering the tips of the pusher bars in the longitudinal direction.

Strekopytov 3,252,643 describes a C-clamp instrument that is really two instruments side-by-side. The replaceable magazine has two rows of staples separated from a third row. The instrument is fired once to apply two rows of staples, the tissue is then manipulated, and the instrument is fired again to apply the third row of staples.

As is apparent from the prior art, several issues arise in designing drive members for driving a plurality of surgical staples. In particular, failure to effectively balance the forces applied to the drive member when ejecting staples may result in a tendency for the staple pusher to bind against the walls of the pusher slot and to jam. Moreover, drive members for driving a plurality of staples tend to offer more resistance to longitudinal movement of the drive cam and they therefore require that the surgeon apply a greater force to operate the stapler. It is desirable that the drive member permit application of a relatively smooth ejection force throughout the operation.

SUMMARY OF THE INVENTION

It has now been found desirable to provide three parallel rows of staples in staggered overlapping arrangement in order to obtain even greater holding strength and improved hemostasis. Prior to the present invention, however, there has not been a drive member capable of simultaneously laying down three rows of staples in a single ejection action.

Accordingly, it is one object of the present invention to provide a surgical staple device member.

It is another object of the present invention to provide a surgical staple drive member capable of driving three staples.

Yet a further object of the present invention is to provide a surgical staple drive member capable of driving three staples in parallel, staggered arrangement.

It is yet another object of the present invention to provide a surgical staple drive member which is less likely to jam and which is easily operable.

These and further objects are realized by providing a single piece integrally constructed staple drive member for a surgical stapling apparatus, the staple drive member being driven by a transversely moving cam, and being capable of driving up to three surgical staples with one stroke of the cam, the staple drive member including:

a body portion having a distal end, a proximal end with at least one camming surface, and three substantially rectangular pusher plates aligned lengthwise in the direction of cam motion.

DETAILED DESCRIPTION OF THE INVENTION

Surgical stapling apparatus employing staple drive members to push surgical staples are described in Green et al. (U.S. Pat. No. 3,490,675) and Green (U.S. Pat. No. 3,499,591) both of which are incorporated by reference herein. The terms "vertical" and "downward" herein are used relatively to refer to a direction transverse to the longitudinal direction as shown in the drawings.

Generally speaking, a surgical stapling apparatus of the type pertaining to the present invention typically includes two elongated jaws configured and dimensioned to receive and clamp body tissue therebetween.

Typically, one jaw bears a cartridge which carries a plurality of drive members and staples arranged in parallel rows flanking a pusher bar having a cam, while the other jaw includes an anvil for forming the staples. The pusher bar travels longitudinally along the cartridge carrying jaw, such that the pusher bar cam transmits substantially vertical motion to the drive members within grooved substantially vertical slots, thereby driving staples through body tissue against the anvil. As shown in U.S. Pat. No. 3,499,591, two parallel rows of staple drive members may be provided, with each staple drive member acting upon two staples. In the foregoing patent, each row of staple drive members lays down two parallel rows of staples. Providing two parallel rows of staple drive members results in two parallel sets of staple rows for a total of four rows of staples, i.e., two rows of staples in each set. As also shown in the foregoing patent, a knife may be provided to cut the tissue between the two parallel sets of staple rows. This latter arrangement is particularly advantageous for joining two hollow organs in communicating relation. As explained above, two problems which may arise with such devices are the unwanted torque which is applied to the drive member, and higher resistance of multiple staple drivers. The present invention avoids these problems by playing one problem off against the other, i.e. by providing a drive member such that the distribution of staple resistance counterbalances the unwanted torque.

Referring now to FIGS. 1A, 1B, 2A, 2B which illustrate the staple drive member of the present invention in perspective view, and in end view, the three-staple drive member 100 comprises a body portion 102 having inclined camming surfaces 104 at the proximal end of the drive member for contacting a transversely moving pusher bar cam. Two camming surfaces are shown, although one would be adequate.

Body portion 102 has three substantially rectangular pusher plates 106A, 106B, 106C aligned such that their respective longitudinally and vertically extending centerlines define three separate and non intersecting planes.

The pusher plates 106A, 106B, 106C are lengthwise aligned in the direction of cam motion and the longitudinal axis of the surgical stapling apparatus. None of the pusher plates 106A, 106B, 106C extend completely from the proximal end of the drive member 100 to the distal end 111B. Rather, they are in staggered orientation with respect to each other such that the two outside pusher plates, 106A and 106C are laterally aligned with each other, each one being on one each of two sides of the staple drive member 100, and each having an end coterminous with the proximal end 111A of the three-staple drive member 100, but the middle pusher plate 106B is displaced from lateral alignment with the side pusher plates 106A and 106C. Middle pusher plate 106B has an end which is coterminous with the distal end 111B of the three-staple drive member 100.

Pusher plates 106A, 106B, 106C each have guide rails 108 on both their proximal and distal ends. Also, each pusher plate 106A, 106B, 106C has a staple cradling notch 110 extending lengthwise along the edge of the pusher plate which contacts the cross bar or back of the surgical staple. The guide rails 108 extend from the notch 110 to the top of the pusher plate.

Figure 1A:
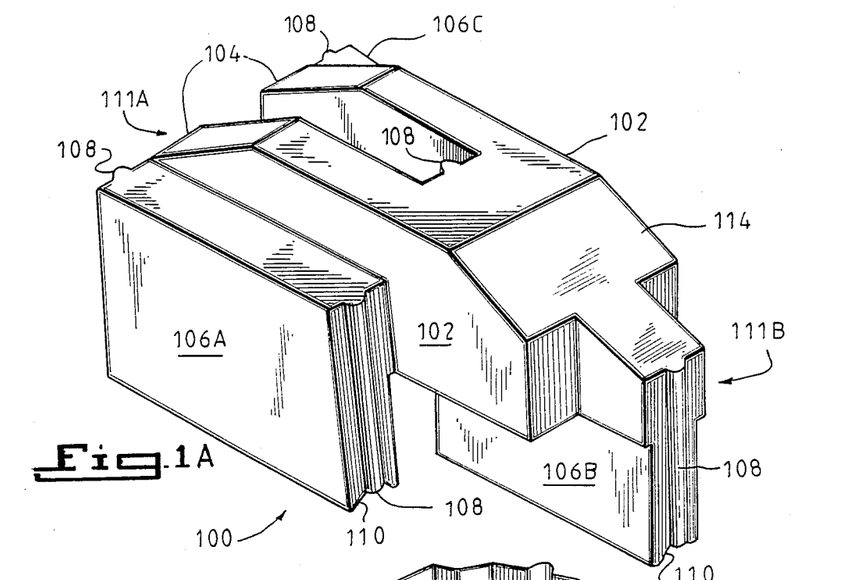
FIG. 1A and 1B illustrate the staple pusher element of the present invention in perspective view.
Figure 1B:
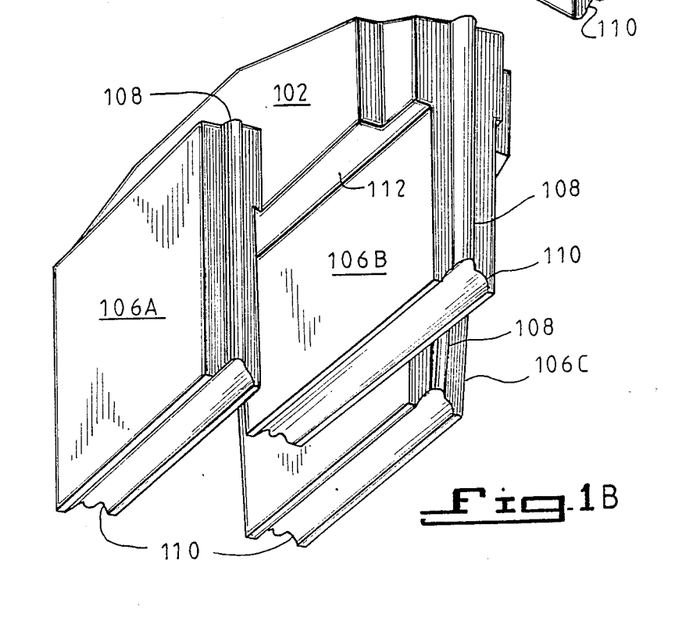
Figure 2A:
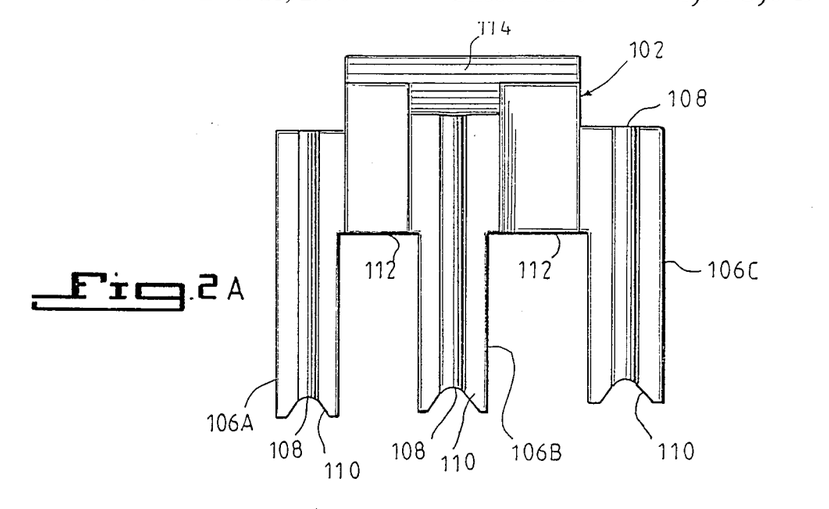
FIG. 2A and 2B illustrate the staple pusher element of the present invention in rear and front view, respectively.
Figure 2B:
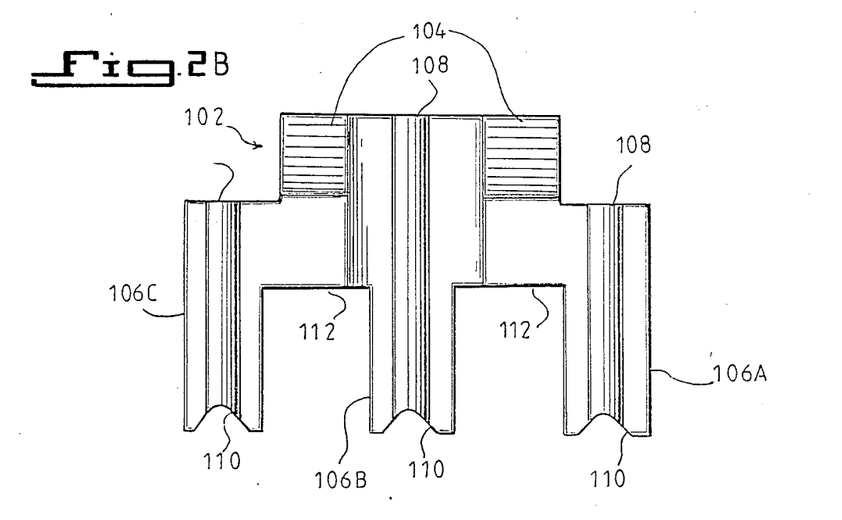

Bevelled surface 114 at the distal end of body portion 102 enables the cam to ride smoothly across the surface of the body portion 102 in both the forward and reverse directions.

Figures 5, 7:
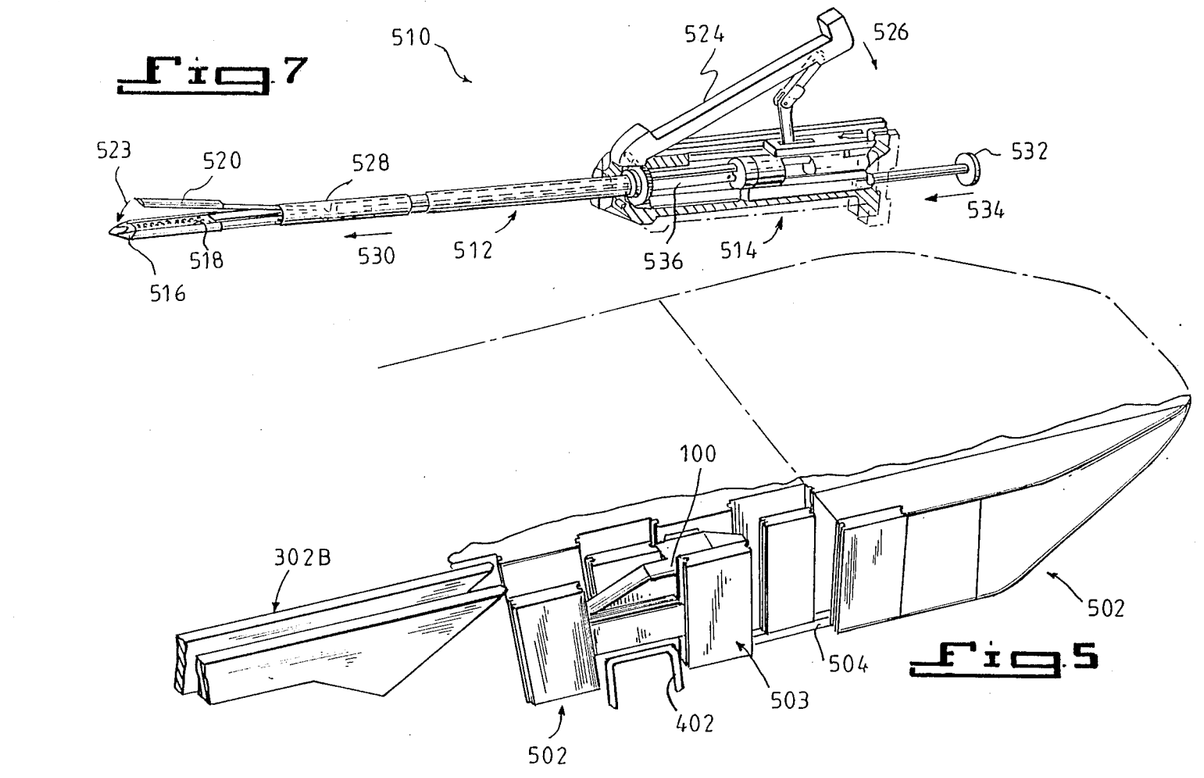
FIG. 5 illustrates in perspective view the surgical staple cartridge containing the staple pusher element.
FIG. 7 is a perspective cut-away view of a surgical stapling apparatus including the staple drive member of the present invention.

Restraining surface 112 prevents the staple drive member 100 from being ejected during operation by abutting the inside surface of the base (504) of the staple holding cartridge (502) (See FIG. 5).

Figure 3:
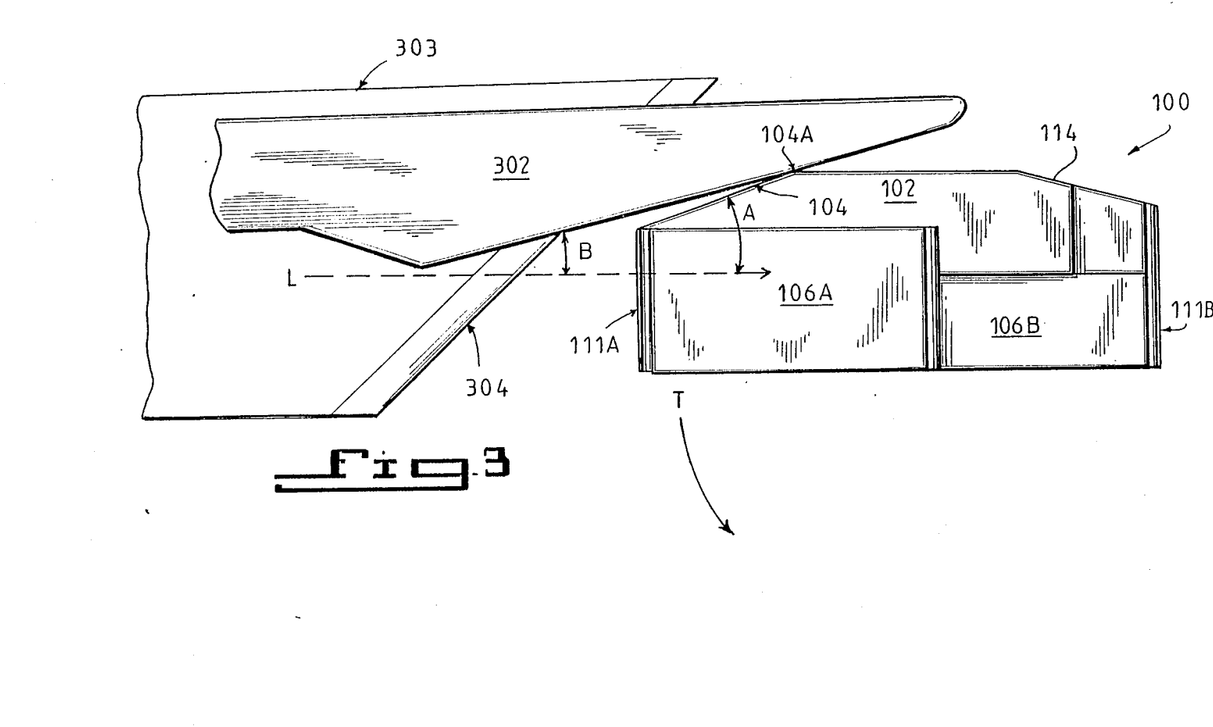
FIG. 3 illustrates a side view of the staple pusher element with cam.

Referring to FIG. 3, cam 302 moves longitudinally in the stapler apparatus in the direction shown by arrow L. Cam 302 approaches the proximal end 111A of the staple drive member 100 and contacts the inclined camming surface 104 at the point 104A. As can be seen from the illustration the angle B between the edge of cam blade 302 and the direction of travel L is less than angle A between the camming surface 104 and direction of travel L. This difference in angles is to prevent jamming of the apparatus which is likely to occur if angle B were larger than angle A. Angle A of the camming surface is optimally about 20° deviation from horizontal and the beveled surface 114 at the distal end is about 15° deviation from horizontal.

As can be seen in the illustration, when cam 302 contacts the camming surface 104, a downward movement is produced in the staple driver member 100 disposed in grooved slots in a staple holding cartridge (see FIG. 5). But there is also some undesired torque induced in the staple driver as generally illustrated by arrow T. This torque could cause rotation of the staple driver 100 within the grooved slot which could result in jamming. But with the staple driver 100, the undesired torque is counterbalanced by greater resistance at the proximal end 111A of the staple driver. This is so because there are two staples at the proximal end, one each driven by pushers 106A and 106C, and they both offer resistance whereas the distal end 111B has only one staple, which is driven by pusher 106B. The staple driver 100 may also operate with only two staples provided that both of them were at the proximal end driven by side pusher plates 106A and 106C. If the driver 100 had only one staple and that were driven by the middle pusher 106B, the staple driver 100 would have a much higher likelihood of jamming.

FIG. 3 also illustrates a knife member 303, which is an elongated member having a distal cutting edge 304. The knife is movable in the same direction of motion as the cam means in response to movement of the actuating means for driving the cam bar. The knife member is located between the two sets of parallel staple rows and moves longitudinally between them to create an incision in body tissue in a known manner which is sealed on both sides by the staples.

Figures 4A, 4B:
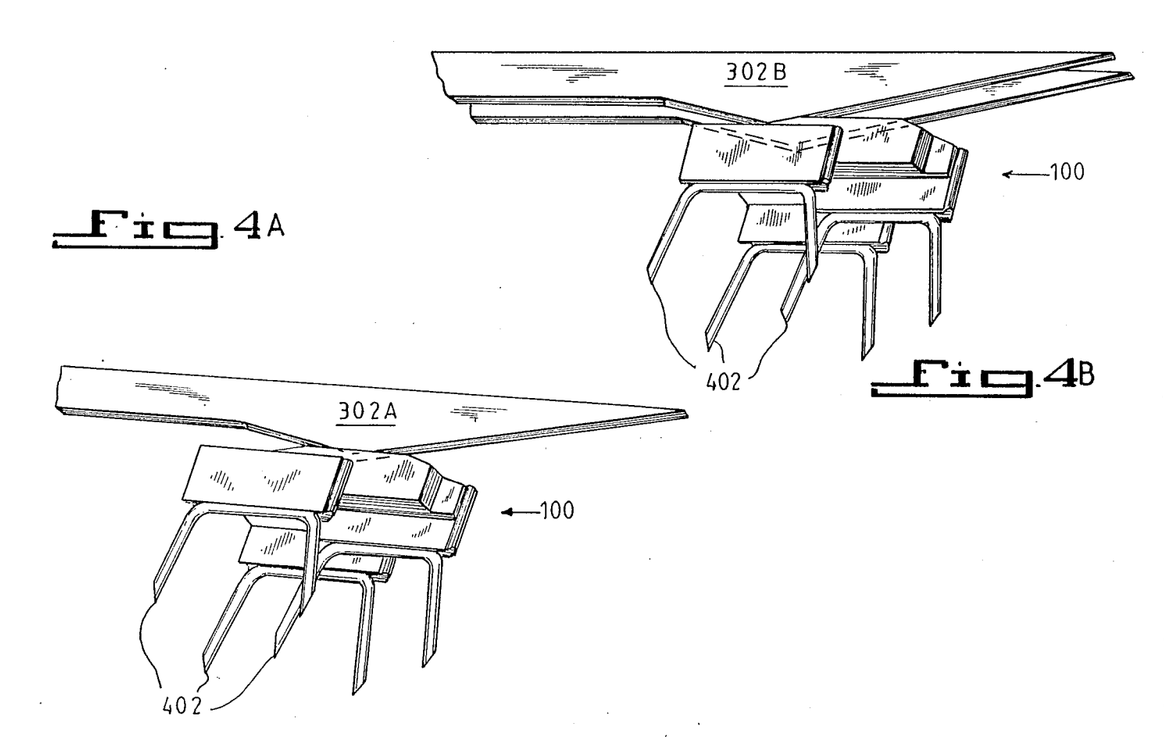
FIG. 4A and 4B illustrate respectively single and double cam operation of the staple pusher element.

FIGS. 4A and 4B illustrate the staple driver of the present invention 100 in conjunction with single and double blade cams 302A, 302B, respectively. Either type cam may be used in a surgical stapler to actuate the staple driver 100 thereby pushing staples 402. Preferred, though, is the double bladed cam 302B. Cams are generally made of a high strength relatively rigid material such as stainless steel and are actuated by mechanisms which are well known in the art.

FIG. 5 illustrates a staple holding cartridge 502 of a surgical stapling apparatus. Such a cartridge provides a means for holding and driving staples 402. Cartridge 502 comprises a body having a base 504 and uprights 503 which are arranged so as to form grooved slots for staple driver 100. Double bladed cam 302B moves longitudinally down the cartridge impelling, in turn, one after another of the staple drivers 100. (Only one staple driver is illustrated. However in usual operation, all of the grooved slots will be occupied by staple drivers 100 and staples 402).

Figure 6:
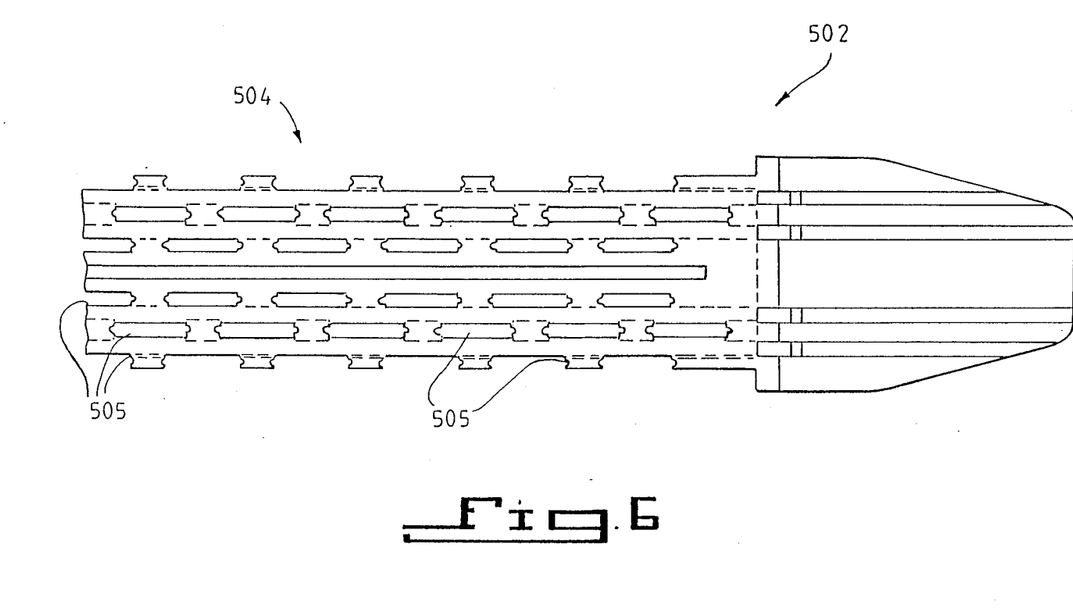
FIG. 6 illustrates a bottom view of the surgical stapler cartridge.

FIG. 6 illustrates a bottom view of the base 504 of the cartridge 502. Elongated apertures 505 provide egress for the staples. The surrounding structure of the base provides a means for preventing the staple driver 100 from also being ejected. When the three-staple drive member 100 has been driven down by the cam 302B, the restraining surface 112 comes into abutment with the inside surface of base 504, thereby preventing the staple drive member 100 from falling out of the cartridge.

The three-staple drive member 100, may be injection molded as a single piece from a high strength polymeric resin, such as (Delrin TM) acetal. The staple drive member 100 may be of any size which is appropriate to its function of driving staples. Typically, such drive members are between 0.1 and 0.2 inches in length, about 0.075 inches in height, and about 0.10 to 0.15 inches in width.

By way of example and not limitation, there is shown in FIG. 7 a surgical stapling apparatus 510 in which the staple drive member in accordance with the present invention may find application. Surgical stapler 510 includes an endoscopic portion 512 and a handle portion 514. The endoscopic portion is intended to be inserted into the body through a narrow diameter opening or tube, on the order of about 10 millimeters, with control of the stapling operation exercised by handle portion 514. Lower jaw 516 is fixed relative to endoscopic portion 512 and carries a cartridge 518 containing staples and staple drive members in accordance with the invention (not shown). Cartridge 518 may also include a knife. Upper jaw portion 520 is movably mounted, as by a hinge, relative to endoscopic portion 512 so as to be closable in the direction of arrow 522 toward lower jaw 516. In operation, lever handle 524 is closed in the direction of arrow 526 to advance collar 528 by appropriate mechanical advantage in the longitudinal direction of arrow 530 in order to close jaws 518,520, clamping body tissue therebetween. Thereafter, handle 532 is longitudinally advanced in the direction of arrow 534 in order to advance drive bar 536 longitudinally through endoscopic portion 512. One or more pusher cams are connected to drive bar 536 and advance simultaneously therewith in the longitudinal direction relative to cartridge 518 in order to drive a plurality of three staple drive members constructed in accordance with the invention, thereby ejecting staples from the cartridge. The ejected staples penetrate through the body tissue and are formed closed against the anvil of upper jaw 520.

Although the proceeding specification contains many specifics, these specifics should not be construed as limitations of the invention, but as exemplifications of preferred embodiments thereof. Those skilled in the art will envision many variations that are within the scope and spirit of the invention as defined by the claims appended hereto.

What is claimed is:

1. A surgical stapling apparatus comprising:
   a cam means which is longitudinally movable through the surgical stapling apparatus and which has a camming edge for contacting a staple drive member;
   actuating means including at least one drive bar for moving said cam means; and,
   a cartridge including a plurality of staple drive members, each said drive member having a body portion including a distal end, a proximal end with at least one camming surface configured and dimensioned to engage said camming edge of said cam means, and three substantially rectangular pusher plates aligned in the direction of motion of said cam means wherein the respective longitudinally and vertically extending centerlines of said three pusher plates define three separate and non-intersecting planes.

2. The surgical stapling apparatus of claim 1 wherein said three substantially rectangular pusher plates comprise:
   (i) two side pusher plates laterally aligned with each other, each side pusher plate having an end coterminous with the proximal end of the staple drive member, said side pusher plates being disposed on opposite sides of said body portion, and
   (ii) a middle pusher plate having an end coterminous with the distal end of the staple drive member.

3. The surgical stapling apparatus of claim 2 wherein each said pusher plate further includes a notch for cradling a cross bar of a staple.

4. The surgical stapling apparatus of claim 3 further comprising an anvil movable between an open position and a closed position aligned with and against said cartridge, said staple drive members ejecting staples from said cartridge against said anvil when said staple drive members are driven by said camming means.

5. The surgical stapling apparatus of claim 4 further comprising a knife member movable in response to said actuating means in the direction of motion of said cam means.

6. A staple drive member for a surgical stapling apparatus, said staple drive member being driven by a cam which is movable longitudinally through the apparatus in a direction substantially transverse to the direction of movement of the staple drive member, and said staple drive member being capable of driving up to three surgical staples with a single stroke of the cam, said staple drive member comprising:
   a body portion having a distal end, a proximal end with at least one camming surface for being contacted by said cam, and three substantially rectangular pusher plates aligned in the direction of cam motion wherein the respective longitudinally and vertically extending centerlines of said three pusher plates define three separate and non-intersecting planes.

7. The staple drive member of claim 1 wherein said three substantially rectangular pusher plates comprise:
   (i) two side pusher plates laterally aligned with each other, each of said side pusher plates having an end coterminous with the proximal end of the staple drive member, said side pusher plates being disposed on opposite sides of said body portion, and
   (ii) a middle pusher plate having an end coterminous with the distal end of the staple drive member.

8. The staple drive member of claim 6 wherein said distal end of the body portion has a bevelled surface.

9. The staple drive member of claim 6 wherein said staple drive member is constructed of a polymeric resin.

10. The staple drive member of claim 9 wherein the polymeric resin is acetal.

11. The staple drive member of claim 6 wherein each said pusher plate is provided with guide rails.

12. The staple drive member of claim 11 wherein said guide rails are disposed at the proximal and distal ends of each said pusher plate.

13. The staple drive member of claim 6 wherein said pusher plates each additionally have a notch for cradling the back of a staple.

14. In combination:
(a) a plurality of staple drive members each comprising a body portion having a distal end, a proximal end with at least one camming surface for being contacted by a movable cam means, and three substantially rectangular pusher plates aligned lengthwise in the direction of cam motion wherein the respective longitudinally and vertically extending centerlines of said pusher plates define three separate and non-intersecting planes; and
(b) a surgical stapling apparatus including cam means which is longitudinally movable through the surgical stapling apparatus, said cam means having a camming edge for contacting said camming surface of the staple drive members, said stapling apparatus including at least one drive bar for actuating said cam means, a cartridge having a plurality of slots adapted to receive said staple drive members, and an anvil member.

* * * * *